(12) United States Patent
Van Dreden

(10) Patent No.: US 6,251,619 B1
(45) Date of Patent: Jun. 26, 2001

(54) PROCESS FOR DETERMINING A RESISTANCE TO ACTIVATED PROTEIN C

(75) Inventor: Patrick Van Dreden, Maisons-Alfort (FR)

(73) Assignee: Societe Diagnostica Stago, Asnieres (FR)

( * ) Notice: Subject to any disclaimer, the term of this patent is extended or adjusted under 35 U.S.C. 154(b) by 0 days.

(21) Appl. No.: 09/242,029

(22) PCT Filed: Jun. 5, 1998

(86) PCT No.: PCT/FR98/01148

§ 371 Date: Feb. 5, 1999

§ 102(e) Date: Feb. 5, 1999

(87) PCT Pub. No.: WO98/55875

PCT Pub. Date: Dec. 10, 1998

(51) Int. Cl.[7] .................................................. C12Q 1/56
(52) U.S. Cl. .................................................. 435/13
(58) Field of Search ................................. 435/13

(56) References Cited

U.S. PATENT DOCUMENTS

| | | | |
|---|---|---|---|
| 5,318,899 | 6/1994 | Scarborough et al. | 435/69.6 |
| 5,342,830 | 8/1994 | Scarborough | 514/12 |
| 5,968,902 * | 10/1999 | Scarborough et al. | 514/9 |

FOREIGN PATENT DOCUMENTS

| | | |
|---|---|---|
| 2162531 * | 5/1996 | (CA) . |
| WO 93/10261 | 5/1993 | (EP) . |
| WO 96/04560 | 2/1996 | (EP) . |
| 0711 838 A1 | 5/1996 | (EP) . |
| WO 96/15457 | 5/1996 | (EP) . |
| 002057016 | 12/1990 | (HU) . |
| 002057015 | 3/1989 | (SU) . |

OTHER PUBLICATIONS

R.M. Bertina et al., Nature, 1994, 369, pp. 64–67.
B. Dahlback et al., Proc. Natl. Acad. Sci. USA, 1993, 90, pp. 1004–1008.
193596h, J. Amiral et al., Chemical Abstracts, 1987, 107, p. 336.

* cited by examiner

Primary Examiner—Ralph Gitomer
(74) Attorney, Agent, or Firm—Evenson, McKeown, Edwards & Lenahan, P.L.L.C.

(57) ABSTRACT

A process for determining a resistance to activated protein C of a test specimen of human plasma following the steps of: (1) mixing together (a) the test specimen of human plasma, (b) a reactant deficient in factor V which supplies at least most of the coagulation factors other than factor V, and (c) the venom of *Crotalus viridis helleri* which specifically activates factor X to Xa, and incubating the mixture of (a), (b) and (c) for at least one minute at a temperature of between 10 and 45° C.; (2) introducing into the incubated mixture(i) $Ca^{2+}$ or (ii) $Ca^{2+}$+exogenic activated protein C; and (3) determining the coagulation time (i) in the absence of activated protein C and (ii) in the presence of activated protein C. Steps (1) to (3) are repeated, but replacing, in step (1), the test specimen with a normal plasma as control and correlating resistance to activated protein C by comparing the determinations made in steps for the test specimen and for the normal plasma. The initiation of coagulation is caused by activating factor X to Xa using the venom of *Crotalus viridis helleri* in the presence of (i) $Ca^{2+}$ or (ii) $Ca^{2+}$+ exogenic activated protein C.

18 Claims, 1 Drawing Sheet

PROCESS FOR DETERMINING A RESISTANCE TO ACTIVATED PROTEIN C

This application is a 371 of PCT/FR 98/01148 filed Jun. 5, 1998 which claims priority to France 97 07 041 filed Jun. 6, 1997.

FIELD OF THE INVENTION

The present invention relates to a new use of a particular snake venom, the venom of *Crotalus viridis helleri* (this venom is referred to hereinafter as CVH), in the field of determining the reactivity of the activated protein C, this determination including that of the activity of the functional protein C and that of resistance to the activated protein C (activated protein C is called APC herein and resistance to APC is abbreviated as APC-R; the other abbreviations used are defined further below). The invention likewise relates to a method for determining APC-R, using CVH and a dosing kit enabling this method to be used.

PRIOR ART

The study of hereditary thrombophiliacs has shown that APC-R is mainly associated with a mutation on the gene coding for factor V. This mutation, called "Leiden's mutation," "mutation R506Q" or "mutation $^{506}R \rightarrow ^{506}Q$," appears in the sequence of the amino acids of human factor V by the replacement of Arg by Gln in position 506, and favors the appearance of thromboses, often venous (in the lower body members with, in some cases, pulmonary embolism). See particularly in this connection the publications of R. M. Bertina et al., *Nature,* 1994, 369, pages 64–68, of M. Kalafatis et al., *J. Biol. Chem.* 1994, 269, pages 31869–31880, of H. De Ronde et al., *Thromb. Haemost.,* 1994, 72, pages 880–886, of P. J. Svensson et al., *N. Engl. J. Med.,* 1994, 330, pages 517–522, of B. Dahlbäck et al., *Proc. Natl. Acad. Sci. USA,* 1993, 90, pages 1004–1008, and of B. Dahlbäck et al., *Proc. Natl. Acad. Sci. USA,* 1994, 91, pages 1396–1400.

Other factor V anomalies can be at the origin of APC-R. In particular, it is possible that an untimely cleavage in position 306 (i.e., $^{306}$Arg) of the amino acid sequence of factor V and/or Va is one of the other possible causes of APC-R.

The determination of APC-R was employed initially (particularly by an APTT, KCCT or other such test) to detect the existence of a thrombotic disorder by comparing the coagulation time, which is prolonged by the addition of APC, of a control plasma with one that is shorter in case of an irregularity in relation to the preceding one, of a sample of human plasma to be tested with APC added.

See in this connection: C. A. Mitchell et al., *N. Engl. J. Med.,* 1987, 317, pages 1638–1642, L. Amer et al., *Thromb. Res.,* 1990, 57, pages 247–258, and B. Dahlbäck et al., *Thromb. Haemost.,* 1991, 65, Abstract 39, page 658.

The only kit presently available on the market (it is sold by the name of "Coatest APC-Resistance" by the firm of Chromogenix) uses the process described in the disclosure of B. Dahlbäck et al., *Thromb. Haemost.,* 1991, 65, Abstract 39, page 658, referred to above and explained in WO-A-9310261, and the article by B. Dahlbäck et al., *Proc. Natl. Acad. Sci. USA,* 1993, 90, pages 1004–1008, referred to above. This process comprises mixing one volume of the plasma to be tested or of the control plasma with one volume of the APTT reactant [PL +surface activator (silica, kaolin or glass)], incubation for 4 minutes at 37° C., then starting coagulation by means of one volume of a solution of $CaCl_2$, on the one hand, or of one volume of a solution of $CaCl_2$ and APC, on the other.

This process is unsatisfactory in that, being sensitive particularly to the presence of factor VIII, heparin, PS, CAC's and VKA's, it gives too many false negative and false positive results. Improvements have therefore been proposed in WO-A-9615457, WO-A-9604560 and EP-A-0711838.

WO-A-9615457 proposes an APC-R determination in which the plasma to be tested is placed in contact with a procoagulant reactant (tissue factor in this case) and a VdfP; then, after incubation, coagulation is started with $CaCl_2$ or $CaCl_2$+APC, the variation of the coagulation time being then determined by comparison with a control plasma.

WO-A-9604560 aims at an improved technique for detecting APC-R. This technique is based on the use of an exogenic reactant that specifically activates the V factor to Va, to supplement an activation of the coagulation either by the transformation X→Xa, or by the transformation of prothrombin to thrombin by a mechanism depending on the V factor.

WO-A-9604560 recommends particularly,
- as an exogenic reactant, a snake venom such as the venom of Naja nivea to activate V to Va, and
- for the supplemental activation: either RVV-X to activate X to Xa, either a snake venom (or venom extract), such as the venoms of *Pseudonaja textilis, Notechis scutatus* or *Oxyurnus scutellatus,* for the activation of prothrombin to thrombin by a mechanism depending on factor V.

For the determination of APC-R, EP-A-0711838 recommends a process comprising;
(a) the mixing of a plasma to be tested with a reactant A with a low content of factor V, particularly VdfP,
(b) the addition of a reactant B that directly or indirectly activates factor V to Va, particularly a viper venom such as RVV (with by its RVV-V fraction induces the activation of V to Va and which by its RVV-X fraction induces the activation of X to Xa) or the venom of *Echis carinatus* (which induces the activation of prothrombin to thrombin and then activates V to Va indirectly).
c) the addition of a reactant C permitting degradation of the Va factor, viz., APC [(or the mixture PC +activator (particularly ACC)], and
d) the addition of reactants permitting the determination of the residual activity of the Va factor, on the condition that the proportion of the volume of the plasma sample to be tested with respect to the total volume is no more than 20%, advantageously less than or equal to 10% ("the content of the sample volume being a maximum of 20%, but preferably less than or equal to 10%," according to claim 1, page 13, lines 39–40 of EP-A-0711838).

This process has the disadvantage of calling for volumes of plasma (to be tested, or plasma for control), of reactant A and of reactant B which are all three different. This circumstance does not make it easy to measure the coagulation time with a fully automatic apparatus.

The aforesaid processes of WO-A-9604560 and EP-A-0711838 make it possible to relieve most of the disadvantages of the "Coatest APC-Resistance." However, these two documents neither describe nor suggest the use of the particular snake venom of the invention, viz. CVH, to initiate coagulation at the level of the X factor by the transformation X→Xa.

The only effective technique today for determining APC-R is based on molecular biology (MB). It is lengthy, fussy, burdensome and calls for prepared material and highly qualified personnel. Moreover, its employment must satisfy Article L. 145–15 of French Law No. 94–653 of Jul. 29, 1994 which requires obtaining the written consent of the persons for whom a genetic study is undertaken.

THE SUMMARY OF THE INVENTION

It is intended to provide a new technical solution for the determination of APC-R which (i) will be simple at the level of practice, (ii) will be at least as effective as those considered in the above-mentioned documents WO-A-9604560 and EP-A-0711838, and (iii) is based on initiating coagulation at the X factor (i.e., transformation X-Xa) whose importance has been recognized in WO-A-9604560 (see page 5, lines 1–12).

The aim is to improve sensitivity by reducing the number of false positive and false negative results. With this in mind it is proposed to employ an APC-R determination process by classical mechanisms, but with the peculiarity that a new reactant or means is used to initiate coagulation by the transformation X-Xa, this means or reactant improving sensitivity.

The new technical solution according to the invention is based on the selection of a particular activator to initiate coagulation at the X factor (i.e., X→Xa). This particular activator is a snake venom, namely CVH.

According to a first aspect of the invention, a new use for a snake venom is announced, for starting coagulation by activating the X factor to Xa for the purpose of determining the reactivity of the activated protein C, particularly the functional activity of the protein C (PC) of a human plasma being tested, the said use being characterized in that it resorts to the venom of *Crotalus viridis helleri* as the coagulation initiating substance, in the presence of $Ca^{2+}$, at the X factor, the said venom activating X selectively to Xa without being influenced by the presence or absence of other coagulation factors.

According to a second aspect of the invention, a new method of determining the APC-R of a test specimen of human plasma, the method, which employs the initiation of coagulation at the X factor by means of a snake venom in the presence (i) of $Ca^{2+}$ or (ii) a mixture of $Ca^{2+}$ and exogenic APC, then the evaluation of the coagulation time, (i) in the absence of APC and (ii) in the presence of APC, respectively, in comparison with a normal plasma, being characterized by comprising steps consisting of (1) bringing into contact
   (a) a specimen of the human plasma to be tested,
   (b) a reactant deficient in V factor (VdfR) as a product furnishing most (preferably all) of the coagulation factors other than V factor, and
   (c) CVH as a product specifically activating X to Xa, and incubating the mixture thus obtained for at least 1 minute at a temperature between 10 and 45° C., preferably for 3 to 5 minutes at a temperature of 35 to 40° C. and, better, for 4 minutes at 37° C.;
(2) introducing into the mixture thus incubated (i) $Ca^{2+}$ or (ii) $Ca^{2+}$+exogenic APC, respectively;
(3) evaluating the coagulation time (i) in the absence of APC and (ii) in the presence of APC, respectively;
(4) repeating steps (1) to (3) by replacing, in step (1), the test specimen of human plasma with a normal plasma as control, and
(5) estimating APC-R by comparing the evaluations obtained in steps (3) and (4).

According to a third aspect of the invention, a variant of this process is offered, which can be performed directly without the need, on the one hand, to make a comparison with a control plasma (normal plasma or pool of normal plasmas) and, on the other hand, to perform a measurement without the addition of APC. This variant comprises steps (1), (2, ii) and (3, ii) of the principal process, on the one hand, then the estimation of APC-R by comparing the coagulation time (T) obtained in step (3, ii) to an experimentally determined reference coagulation time (To) (having a value of approximately 110 s on a statistical basis), on the other hand, T<To indicating generally that the test specimen of human plasma has a resistance to activated C protein, and T>To indicating generally that the test specimen of human plasma has no resistance to activated C protein.

This variant is advantageous in that the determination of APC-R is simpler, less expensive and easier to automate than the main process considered above.

According to another aspect of the invention, a dosage kit is offered which includes:

a first reactant which is a plasma deficient in V factor, a second reactant constituted by CVH, and a third reactant constituted by APC in a calcium medium.

ABBREVIATIONS

For convenience, the following abbreviations and acronyms have been used in the present description.

ACC Venom of *Agkistrodon contortrix;* this venom is a product which selectively activates PC to APC APC Activated protein C APC-R Resistance to activated protein C (when "plasma APC-R" is involved, it is understood that the plasma is resistant to APC).

APTT Activated partial thromboplastin time

ATIII Antithrombin III

CAC Circulating anticoagulant

CVH Venom of *Crotalus viridis helleri*

KCCT Kaolin-cephalin clotting time

MB Molecular biology test, here employing a coding nucleic probe for a peptide fragment of about ten amino acids comprising $^{506}Q$, and the detection of the mutation by hybridization of the probe after amplification (by PCR) of the corresponding region of the DNA MB+ Identifies a plasma in which the V factor comprises the mutation R506Q (i.e., plasma "positive" according to the MB test)

MB− Identifies a plasma in which the V factor does not comprise the mutation R506Q (i.e., plasma "negative" according to the MB test)

OKB Owren-Koller buffer; this is a veronal buffer

PB Prionex buffer (buffer containing the polypeptide fraction with pork collagen removed)

PC Protein C

PCR Polymerase chain reaction

PL Phospholipids

PS Protein S

RVV Russel viper venom (*Vipera russeli*); this venom activates factor V to Va and factor X to Xa RVV-V Purified fraction of RVV activating factor V to Va RVV-X Purified fraction of RVV activating factor X to Xa VdfP Plasma deficient in factor V VdfR Reactant deficient in factor V
VKA Vitamin K antagonist

DETAILED DESCRIPTION OF THE INVENTION

Figure 1:
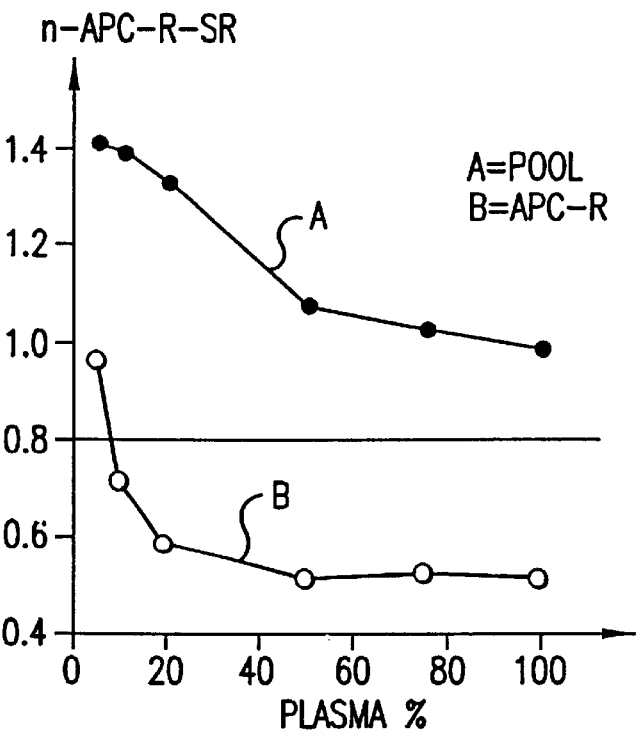
FIG. 1 shows the variation of the normalized ratio N-APC-R-SR, which is defined further below and represented on the ordinates in relation to the concentration (% v/v) of the plasma (control pool or APC-R plasma) in a mixture of plasma+VdfP, this concentration being represented on the abscissae.

The use of the particular venom CVH according to the invention makes it possible to know the reactivity of APC, and in particular the functional activity of PC on the one hand and APC-R on the other. Of course, the determination of APC-R is more important at the diagnostic level than that of the functional activity of PC. Consequently, the determination of the functional activity PC is only secondary in relation to the determination of APC-R which makes it possible to estimate the risk of thrombosis in the patient being tested.

CVH is a commercial product available on the market. It can be obtained in purified and lyophilized form from the Sigma company. Prior to the invention this venom was used mainly for the production of an antiserum against snakebite of *Crotalus viridis helleri*. In practice, lyophilized CVH will be diluted with PB to a concentration of 0.1 to 0.15 $\mu$g/ml (preferably a concentration of 0.12 $\mu$g/ml, which corresponds to an end concentration, in the employment of the process, of 0.03 $\mu$g/ml).

The reactant VdfR is chiefly a plasma VdfP. The expression "deficient in factor V" signifies a reactant (VdfR) or a plasma (VdfP) which is either essentially of reduced factor V content or contains no factor V. VdfR or VdfP are used according to the invention as a substrate plasma which can be of synthetic, animal or human origin. Advantageously, a VdfP containing no factor V will be employed, and will be obtained by immunodepletion. To prevent any interference from the anti-phospholipids, particularly those of lupus, it is recommended that VdfR or VdfP be enriched with PL.

According to one particular embodiment, in step (1) a test specimen of human plasma obtained by treatment with trisodium citrate (when it was taken) is used, centrifuged at 3500 g for about 15 minutes, and diluted with OKB. The normal plasma used as control in step (4) is obtained in the same way.

In a practical way, bearing in mind the notations APC-R-SR and N-APC-R-SR proposed in the aforementioned article of H. De Ronde et al., in step (3) and in step (4) sensitivity to APC is evaluated for the test specimen of human plasma and for the control plasma, the sensitivity being the ratio (called APC-R-SR) of the coagulation time in the presence of APC to the coagulation time without APC:

$$\text{APC-R-SR} = \frac{\text{coagulation time in presence of APC}}{\text{coagulation time in the absence of APC}}$$

and in that in step (5) APC-R is reckoned by the normalized ratio (called N-APC-R-SR) of the sensitivity to APC of the test specimen of human plasma to the APC sensitivity of the normal control plasma:

$$\text{N-APC-R-SR} = \frac{(\text{APC-R-SR}) \text{ specimen}}{(\text{APC-R-SR}) \text{ control plasma}}$$

In the process of the invention, a value of the normalized ratio N-APC-R-SR greater than 0.80 indicates that the human test specimen generally offers no resistance to the activated protein C, and a value of the normalized ratio N-APC-R-SR less than 0.80 indicates that the test specimen generally does offer resistance to the activated protein C. The normal plasma used as control is advantageously a pool of normal human plasmas.

When the value of the normalized ratio is within the gray area ($0.72 \leq$ N-APC-R-SR $\leq 0.90$) for a concentration x (% v/v) of a plasma specimen in a mixture of x (plasma) +y (VdfP) or x +y=100%, it is recommended to increase the concentration of the plasma, that is, inversely, to reduce the concentration of VdfP in the said mixture x+y. Thus a value of N-APC-R-SR is obtained which is outside of the gray area (see FIG. 1 below).

Advantageously, identical volumes of each of the reactants will be used according to the invention, viz.: the human test plasma (preferably diluted 1:10 in OKB), VdfR (or VdfP), $CaCl_2$ solution, $CaCl_2$+APC solution, control plasma (or control plasma pool), and solution (or dilution) of CVH (preferably CVH in water containing 1% v/v of PB).

The evaluation of APC-R in steps (3), (4) and (5) is of a type known in the prior art, which corresponds to the rate of conversion of a substrate. The coagulation time is measured either directly (particularly by means of a coagulometer), recording the instant corresponding to the thrombin formation generated in the reacting system, the substrate being then prothrombin. The substrate preferred according to the invention is VdfP.

The dosage kit or set according to the invention will advantageously include a VdfP enriched with PL. The kit can also contain $CaCl_2$ for preparing the aqueous solution of $CaCl_2$ at the concentration required in order to supply the $Ca^{2+}$ ions that induce coagulation. The timer is started when the $Ca^{2+}$ ions are introduced.

According to the preferred embodiment of the process of the invention:

in step (1),
  (A) the human blood test specimen, diluted with OKB to a concentration equal to or more than 1/20 v/v, preferably to a concentration of 1/10 v/v.
  (B) a human plasma deficient in factor V and enriched with PL, as the reactant VdfR, and
  (C) the venom of *Crotalus viridis helleri* are brought into contact and incubated for 4 minutes at 37° C.;
in step (2), into the mixture thus incubated, (i) $Ca^{2+}$ or (ii) the mixture of $Ca^{2+}$ plus exogenic APC are placed;
in step (3) the APC sensitivity of the test human plasma to APC is evaluated;
in step (4), all of steps (1) to (3) where, in step (1), the test specimen of human plasma was replaced with a normal human plasma, so as to evaluate the APC sensitivity of the normal human plasma, and
in step (5), the APC-R is estimated by the normalized ratio n-APC-R-SR , and a value of the ratio greater than 0.80 (preferably, N-APC-R-SR>0.90) indicates that the test specimen of human plasma has no resistance to the activated protein C, and a value of the ratio n-APC-R-SR of less than 0.80 (preferably N-APC-R-SR<0.72) indicates that the test specimen of human plasma does offer resistance to the activated protein C, the normal plasma used as control being advantageously a pool of normal human plasmas.

As it will be shown hereinafter, the process of the invention is specific and effective. It provides "intra-test" coefficients of variation of less than 3%, and "inter-test" coefficients of variation of less than 5%. Moreover, it is insensitive to the rates of factors of the intrinsic pathway, to fractionated heparins of low molecular weight, to the rates of PS, to the rates of factor VIII, to the CAC's, to the VKA's and to the mutation 20210A of prothrombin.

The variant of this process, which is recommended in consideration of its ease of practice, its lower cost and its suitability for being more easily automated on present-day machines, is an improved process.

According to this variant, therefore, an improved process is offered for determining APC-R in a test specimen of human plasma, the process, which employs the initiation of coagulation at the X factor by means of a snake venom in the presence of a mixture of $Ca^{2+}$ and exogenic APC, and then the measurement of the coagulation time (T), being characterized in that it includes the steps consisting of:

(1a) bringing into contact
  (a) a test specimen of human plasma
  (b) a reactant deficient in factor V (VdfR) as a product providing most (preferably all) of the coagulation factors other than factor V, and
  (c) CVH as a product specifically activating X to Xa, and incubating the mixture thus obtained, for at least 1 minute at a temperature between 10 and 45° C., preferably for 3 to 5 minutes at a temperature of 35 to 40° C., and better for 4 minutes at 37° C.;

(2a) introducing the mixture thus incubated $Ca^{2+}$ and exogenic APC;

(3a) measuring the coagulation time (T) and (4a) estimating APC-R by comparing the coagulation time (T) thus measured with the experimentally determined reference coagulation time ($T_0$) having statistically a value of about 110 s. $T<T_0$ indicates that the human plasma test specimen has a resistance to the activated protein C, and $T >T_0$ indicates that the human plasma test specimen has no resistance to the activated protein C.

The operations set forth above for steps (1), (2, ii) and (3, ii) apply very surely to steps (1a), (2a) and (3a) of the variant of the process of the invention.

From the practical point of view, $T_0$ has a length of 20 s (110±10 s). Thus, when T is greater than 120 s the plasma tested is normal, and when T is less than 100 s the plasma tested it is certainly APC-R.

There is really an interval of doubt (in English: "grey zone") which corresponds closely to the aforementioned interval [$0.71 \leq$N-APC-R-SR$\leq 0.90$ of the principal process] when $100 \times \leq T \leq 120$ s. If the coagulation time measured is in the gray area of doubt (100 s$\leq T \leq$120 s), it is recommended (i) to employ the principal process by increasing the concentration of the plasma (as indicated above), or (ii) to do an MB study which will give an unequivocal result.

The value $T_0$=110 s and especially the gray area 100 s$\leq T \leq$120 s have been determined experimentally on several lots of known human plasmas [normal plasmas (MB−) and APC-R (MB+) plasmas] by bringing into contact for 4 minutes at 37° C. one volume of each plasma to be studied (previously diluted 1:10 in OKB), 1 volume of VdfP enriched with PL and 1 volume of CVH, and introducing into the resultant mixture 1 volume of an APC solution containing $CaCl_2$, and then measuring the time T. For further details see Examples 13 and 14 below.

Other advantages and features of the invention will be better understood from the reading that follows of embodiments and tests. None of these things is restrictive but are given by way of explanation. For the reader's information, it is stated that Examples 1–3 concern obtaining various products and reactants involved according to the invention; examples 4–12 relate to the execution of the process of the invention, and examples 13–14 relate to variants of this process.

EXAMPLE 1
Obtaining the Human Plasma for Testing The plasma is drawn into an 0.102 M solution of trisodium citrate, at the rate of 1 volume of citrate per 9 volumes of blood. The specimen is then centrifuged at 3500 g for 15 minutes at 4° C. It is recommended to perform a double centrifugation at 4° C. so as to eliminate any platelets from the specimen. The separation and collection of the plasma must be performed as quickly as possible after drawing.

After decantation the plasma can be stored at
  2–8° C. for 8 hours.
  15–19° C. for 8 hours, and
  −20° C. for 1 month.

For thawing, the plasma must be thawed at 37° C. in a thermostat-controlled water bath for at least 10 minutes, then homogenized before use. Refreezing a plasma is to be ruled out.

EXAMPLE 2
Obtaining a Control Plasma
The procedure is as indicated in Example 1.

EXAMPLE 3
Preparation and Preservation of the Reactants
First Reactant (R1)
R1 is a lyophilized human plasma immunodepleted of factor V and enriched with PL. The lyophilized product is made into an aqueous composition with 2 ml of distilled water. The resultant solution is homogenized at the ambient temperature (18–25° C.) before use.

This solution is stable at
  18–25° C. for 6 h
  15–19° C. (in the automatic analyzer sold under the trademark "STA" by the Diagnostica Stago company) for 38 h
  2–8° C. for 26 h, and
  −20° C. for 1 month Second Reactant (R2)
R2 is the lyophilizate of CVH. This lyophilized product is made into an aqueous composition with 2 ml of distilled water (which can advantageously contain 1% v/v of PB). The resultant composition is homogenized at the ambient temperature (18–25° C.) before use.

This composition is stable at:
  18–25° C. for 6 h
  15–19° C. in the STA analyzer for 38 h
  2–8° C. for 26 h and
  −20° C. for 1 month.

Third Reactant (R3)
R3 is the activated human protein C in a lyophilized calcium medium. The lyophilizate is poured into 1 ml of distilled water. The resultant solution is homobenized at the ambient temperature (18–25° C.) before use.

This solution is stable at:
18–25° C. for 6 h
15–19° C. in the STA analyzer for 38 h,
2–8° C. for 26 h, and
−20° C. for 1 month.

EXAMPLE 4

Procedure

Identical volumes of the various products and reactants (unless otherwise stated) which are obtained according to Examples 1–3 above) which are involved in the determination process according to the invention. These volumes are between 5 µl and 50 µl. The specifications that follow are those relating to the measurements made with the above-mentioned STA analyzer; the following are thus used:

50 µl of a test specimen of human plasma (or from a pool of normal plasmas), diluted 1:10 in OKB, 50 µl of R1 (i.e., VdfP enriched with PL), 50 µl of R2 (i.e., CHV) and 50 µl of $CaCl_2$ in aqueous solution or of R3 (i.e., $APC+Ca^{2+}$).

In the STA analyzer the human test plasma or pool of normal plasmas, the PL-enriched VdtP, and CVH are combined. The resultant mixture is incubated for 4 minutes at 37° C.

The solution of $CaCl_2$ or the mixture of $CaCl_2+APC$ (i.e., R3) is introduced into the mixture after having preheated each to 37° C. The STA determines the coagulation time per sample tested and the control pool in the presence and in the absence of APC.

The results obtained are directly expressed by the analyzer in the form of the above-mentioned standardized ratio: N-APC-R-SR.

EXAMPLE 5

Determination of the Normal Range

Starting with 30 pouches of plasma supplied by the Centre de Transfusion Sanguine [blood transfusion center], the normal ratio standardized by a normal pool of 25 men and 25 women, as well as the pathological zone in a lot of 15 plasmas MB+ (homozygous and heterozygous APC-R plasmas). It was found that the normal value for the MB− plasmas is such that N-APC-R-SR≧0.80 with the STA analyzer.

EXAMPLE 6

Repeatability within Tests

Starting with 2 APC-R homozygous plasmas (MB+), identified as APC-R 1 and APC-R 2, and with a normal pool serving as control (MB−), 21 determinations were made in triplicate. The results relating to the coefficient of variation are given in the following Table I. They show that the coefficient of variation of the standardized N-APC-R-SR ratio is less than 3%.

TABLE I

|  | Coefficient of variation of N-APC-R-SR | | |
| --- | --- | --- | --- |
|  | Lot 005 | Lot 006 | Lot 007 |
| Pool MB− | 2.08 | 1.94 | 2.25 |
| APC-R 1 (MB+) | 1.64 | 0.96 | 1.32 |
| APC-R 2 (MB+) | 1.60 | 1.82 | 1.57 |

EXAMPLE 7

Day-to-Day Repeatability

To estimate the day-to-day repeatability, a frozen normal plasma (MB−) and 2 pathological plasmas (MB+), one frozen and the other lyophilized, were divided into aliquots and then tested for 10 days with the same lot of reactants on the same STA analyzer. The results are shown in Table II. They show that the coefficient of the day-to-day variation of N-APC-R-SR is less than 5%.

TABLE II

|  | MB + N-APC-R-SR | MB + frozen N-APC-R-SR | MB + lyophilized N-APC-R-SR |
| --- | --- | --- | --- |
| M | 0.93 | 0.51 | 0.56 |
| SD | 0.93 | 0.02 | 0.02 |
| CV % | 3.66 | 3.99 | 4.08 |

Notes:
M: average of 10 tests per plasma
SD: standard deviation from the mean
CV %: Coefficient of variation

EXAMPLE 8

Repeatability Per Lot

The STA analyzer was used to test a normal plasma MB− and a pathological plasma MB+ (heterozygous APC-R plasma) which were divided into aliquots and frozen. Immediately after thawing, each plasma was tested five times in the same series (one flask), and 15 independent series (15 flasks of the same log) were performed. The results given in Table III show that the coefficient of variation is less than 5%.

TABLE III

| T or ratio | Normal Plasma (M−) | | | Pathological Plasma (MB+) | | |
| --- | --- | --- | --- | --- | --- | --- |
|  | M | SD | CV % | M | SD | CV % |
| T w/o APC | 41.93 s | 07.757 | 1.804 | 38.46 s | 0.602 s | 1.564 |
| T with APC | 138.86 s | 5.898 s | 4.247 | 38.46 s | 1.568 s | 2.639 |
| APC-R-SR | 3.31 | 0.157 | 4.738 | 1.54 | 0.035 | 2.236 |
| N-APC-R-SR (median) | 1.230 | 0.052 | 4.242 | 0.575 | 0.010 | 1.807 |

Notes:
T: coagulation time (in seconds)
M: average of the tests
SD: standard deviation from the average
CV: coefficient of variation (expressed in %)

EXAMPLE 9

Lot-by-Lot Repeatability 2 pathological plasmas identified as MB+1 and MB+2 (homozygous plasmas) and a normal plasma MB− were thawed and studied in 3 different lots of the same reactants (average of 5 measurements per test). A second normal plasma identical to the one before was also tested in parallel to determine the ratio N-APC-R-SR. The results shown in Table IV show that the process of the invention is repeatable lot-by-lot.

TABLE IV

| Plasmas tested | n-APC-R-SR | | | |
| --- | --- | --- | --- | --- |
|  | Lot 005 | Lot 006 | Lot 007 | Δ max |
| MB − | 1.17 | 1.10 | 1.07 | 0.10 |
| MB + 1 | 0.54 | 0.52 | 0.55 | 0.03 |
| MB + 2 | 0.55 | 0.52 | 0.54 | 0.03 |

Note: Δ max: maximum variation

According to Table IV, Δ max (as absolute value) is less than or equal to 0.05 for plasmas MV+ and less than or equal to 0.10 for the plasma MB−.

EXAMPLE 10
Influence of the Rate of Factor V

To highlight the specificity of the process of the invention in regard to the V factor, a series of dilutions of a normal pool or of an APC-R plasma in a VdfP, on the one hand and a series of dilutions of the same plasma APC-R in the normal pool, on the other.

Figure 2:
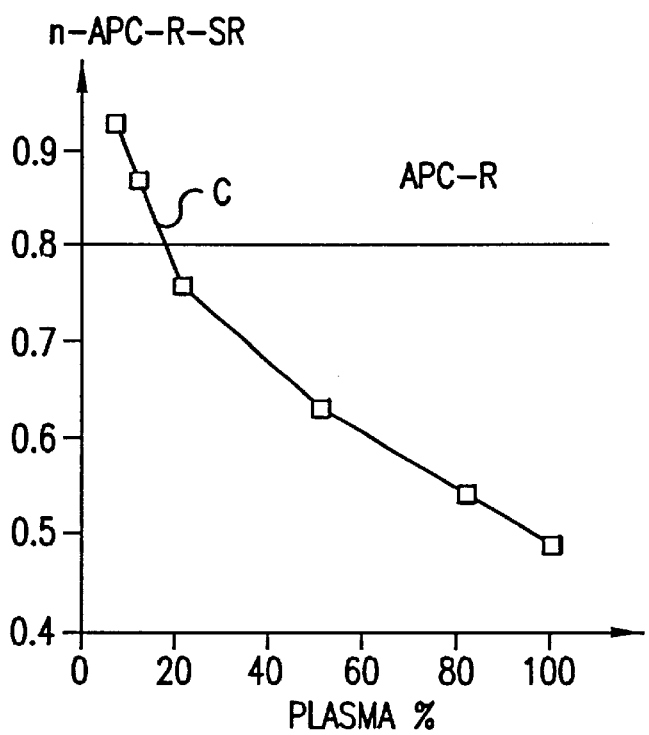
FIG. 2 represents the variation of the said normalized ratio N-APC-R-SR (on the ordinates) with the concentration (% v/v) of an APC-R plasma in a mixture of APC-R plasma plus plasma control pool (on the abscissae).

The results obtained are given in FIGS. 1 and 2.

Curve A in FIG. 1 shows the variation of the standardized ratio N-APC-R-SR according to the concentration (in % v/v) of the pool of normal plasmas in the mixture (pool of normal plasmas)+(VdfP).

Curve B of the FIG. 1 shows the variation of the standardized ratio N-APC-R-SR with the concentration (in % v/v) of the plasma APC-R in the mixture (plasma APC-R)+(VdfP).

Curve C in FIG. 2 shows the variation of the standardized ratio N-APC-R-SR with the concentration (in % v/v) of the same plasma APC-R in the mixture (plasma APC-R)+(pool of normal plasmas).

Curves A and B show that:
- with regard to the dilution of the plasma APC-R in a VdfP, a "positive" result (N-APC-R-SR≦0.71) when the plasma APC-R is in a concentration of 10 to 100% v/v; and
- with regard to the dilution of the normal plasma pool in a VdfP, a "negative" result (N-APC-R-SR≧0.98) when the normal plasma pool is in a concentration of 10 to 100% v/v.

Consequently, curves A and B of FIG. 1 show clearly the specificity of the process of the invention with regard to Leiden's mutation of factor V.

This specificity is confirmed by curve C of FIG. 2 which shows that the dilution of the plasma APC-R in the pool of normal plasmas leads to a "positive" result (N-APC-R-SR>0.80) starting from a concentration of 20% v/v of plasma APC-R in the mixture 9APC-R)+(pool of normal plasmas).

EXAMPLE 11

Comparative Test 1 For comparison, 180 plasmas were tested in the STA analyzer, viz. 60 MB− and 120 MB+ (60 homozygous and 60 heterozygous), identified as MB+ A and MB+ B, using as coagulation initiator either RVV-X according to the teaching of EP-A-0711838 [with a volumetric ratio VdfP/(VdfP+plasma under test)=75%], or CVH according to the invention [with a volumetric ratio VdfP/(VdfP+ plasma under test)=50%]. The results given in Table V show that the process of the invention gives better sensitivity. In this comparative test, a second pool of 50 normal MB− plasmas was used as control.

TABLE V

| Plasmas used | Number of Plasmas Tested | | | | | |
|---|---|---|---|---|---|---|
| | Control by MB | | By the prior art | | By the invention | |
| | + | − | + | − | + | − |
| MB − | 0 | 60 | 0 | 60 | 0 | 60 |
| MB + A | 60 | 0 | 59 | 1 | 60 | 0 |
| MB + B | 60 | 0 | 57 | 3 | 60 | 0 |

EXAMPLE 12
Comparative Test 2

Taking inspiration from the teaching of WO-A-9604560 [viz. a single venom (RVV-X) for the activation of X to Xa], RVV-X was compared with CVH in the determination of APC-R. To this end, two pathological plasmas, identified as APC-R 1 and APC-R 2), diluted 1:10 in OKB, in relation to a pool of normal plasmas, using furthermore two controls: one plasma MB− and one plasma MB+. The results obtained are given in table VI below show that CVH has a discrimination superior to that of RVV-X. For the plasmas APC-R 1 and APC-R2, RVV-X gives a standardized ratio N-APC-R-SR that is within the gray area 0.72≦N-APC-R-SR≦0.90 (0.72 for APC-R 1 and 0.77 for APC-R 2), whereas CVH gives a standardized ratio (0.57 for APC-R 1; 0.58 for APC-R 2) that is decidedly below the minimum (0.72) of the gray area.

TABLE VI

| | Plasmas | | | | |
|---|---|---|---|---|---|
| | Pool normal | MB − control | MB + control | APC-R 1 | APC-R 2 |
| RVVX | | | | | |
| T (s) | 36,6/79.9 | 42,3/86.8 | 40.2/52.4 | 43.4/63.2 | 45.0/70.6 |
| ΔT (s) | 40.3 | 44.5 | 12.2 | 19.8 | 25.6 |
| rs | 2.01 | 2.05 | 1.30 | 1.45 | 1.56 |
| rn | — | 1.02 | 0.64 | 0.72 | 0.77 |
| CVH | | | | | |
| T (s) | 39.3/14.4 | 43.8/118.0 | 42.1/71.1 | 43.0/71.9 | 46.0/78.0 |
| ΔT (s) | 75.1 | 74.2 | 29.0 | 28.9 | 32.0 |
| rs | 2.91 | 2.69 | 1.68 | 1.67 | 1.69 |
| rn | — | 0.92 | 0.57 | 0.57 | 0.58 |

Notes
T: coagulation time (in seconds) without APC/with APC
ΔT: variation of coagulation time T(with APC) - T(without APC)
rs: APC-R-SR
rn: N-APC-R-SR

EXAMPLE 13
Procedure

Identical volumes of the plasma to be studied and of the reactants R1, R2 and R3 obtained from examples 1 and 3 above, respectively. These volumes are between 5 μl and 50 μl. The following procedures are those relating to the work performed by means of the STA analyzer referred to above; thus the following were used:

- 50 μl of human plasma test specimen diluted 1:10 in OKB,
- 50 μl of R1 (i.e., PL-enriched VdfP)
- 50 μl of R2 (i.e., CHV) and
- 50 μl of R3 (i.e., APC+Ca$^{2+}$)

In the STA analyzer, the human plasma to be tested, VdfP enriched with PL, and CVH are combined. The mixture is incubated for 4 minutes at 37° C.

R3 (i.e., CaCl$_2$+APC) , preheated to 37° C., is introduced into the mixture thus obtained. The STA determines the coagulation time (T) for the plasma sample being tested.

Depending on the result obtained, three cases present themselves:
- if T>120 s, the plasma tested is not APC-R [it is a normal plasma (MB−)];
- if 120 s≦T≦100 s, there is doubt (to clear the doubt, the procedure indicated above is followed, or for MB), and
- if T<100 s, the plasma is an APC-R plasma (plasma MB+).

Table III above illustrates such a result, the coagulation time (with APC) of the plasma MB− being 138.86 s, and that of the plasma MB+, 59.42 s. The same is the case with Table VI in regard to the tests involving CVH.

EXAMPLE 14
Effectiveness

Proceeding according to the directions given in Example 13, 582 human plasmas were studied, divided into two lots and each analyzed by MB, lot 1 comprising 398 plasmas (14 MB+ plasmas and 384 MB− plasmas), and lot 2 comprising 184 plasmas (93 MB+ plasmas and 91 MB− plasmas). The results obtained are given in Table VII below, where each coagulation time (T) is stated for periods of 10 s (60 to 160 s) and beyond 160 s.

TABLE VII

| Coagulation Time T (in seconds) | Plasmas Tested Lot 1 (n = 398) (A) | Lot 2 (n = 184) (B) |
|---|---|---|
| 60 < T ≦ 70 | 5 MB+ | 5 MB+ |
| 70 < T ≦ 80 | 8 MB+ | 38 MB+ |
| 80 < T ≦ 90 | 1 MB+ | 37 MB+ |
| 90 < T ≦ 100 | 0 | 12 MB+ |
| 100 ≦ T ≦ 110 | 0 | 1 MB+ |
| 110 < T ≦ 120 | 1 MB− | 0 |
| 120 < T ≦ 130 | 5 MB− | 0 |
| 130 < T ≦ 140 | 42 MB− | 2 MB− |
| 140 < T ≦ 150 | 81 MB− | 5 MB− |
| 150 < T ≦ 160 | 86 MB− | 7 MB− |
| T < 160 | 167 MB− | 77 MB− |

Notes
A: Number and nature of the plasmas of lot 1 that have coagulated
B: Number and nature of the plasmas of lot 2 that have coagulated The results given in Table VII show that the determination technique used (i) gives no false positive and no false negative in lots 1 and 2 (i.e., no MB− plasma is classed among the MB+ plasmas, and conversely no MB+ plasma is classified with the MB− plasmas), and (ii) gives only a limited number (<0.6%) of doubtful values [of the 582 plasmas tested, only 3 plasmas are within the gray area (100×≦T≦120 s), namely; 2 MB− plasmas in lot 1 and 1 MB+ plasma in lot 2].

What is claimed is:

1. A process for determining a resistance to activated protein C of a test specimen of human plasma comprising the steps of:
   (1) mixing together
      (a) said test specimen of human plasma,
      (b) a reactant deficient in factor V which supplies at least most of the coagulation factors other than factor V, and
      (c) venom of *Crotalus viridis helleri* which specifically activates factor X to Xa
   and incubating the resulting mixture of (a), (b) and (c) for at least one minute at a temperature of between 10 and 45° C.;
   (2) introducing into the incubated mixture(i) $Ca^{2+}$ or (ii) $Ca^{2+}$+exogenic activated protein C;
   (3) determining the coagulation time (i) in the absence of activated protein C and (ii) in the presence of activated protein C;
   (4) repeating steps (1) to (3) replacing, in step (1), said test specimen with a normal plasma as control; and
   (5) correlating resistance to activated protein C by comparing the determinations made in steps (3) for said test specimen and (4) for said normal plasma,
   wherein initiation of coagulation is by means of activating factor X to Xa by said venom in the presence of (i) $Ca^{2+}$ or (ii) $Ca^{2+}$+exogenic activated protein C.

2. The process of claim 1, wherein said reactant deficient in factor V is a human or animal plasma deficient in factor V.

3. The process of claim 1, further comprising the step of adding phospholipids to the mixture of step (1).

4. The process of claim 1, wherein said test specimen of human plasma of step (1) is obtained by treatment with trisodium citrate, centrifuged at 3500 g for 15 minutes and diluted with Owen-Koller buffer.

5. The process of claim 1, wherein said normal plasma of step (4) is diluted under identical conditions to those of said test specimen of human plasma.

6. The process of claim 1, further comprising making a comparison of a sensitivity to the activated protein C of said test specimen and said control plasma, said sensitivity being a ratio, called APC-R-SR, of the coagulation time in the presence of the activated protein C (APC) to the coagulation time in the absence of the activated protein C:

$$APC\text{-}R\text{-}SR = \frac{\text{coagulation time in presence of } APC}{\text{coagulation time in absence of } APC}$$

and normalizing the correlation made in step (5) by a standardized ratio, called n-APC-R-SR, of the sensitivity to activated protein C of said test specimen to the sensitivity to activated protein C of the normal control plasma:

$$n\text{-}APC\text{-}R\text{-}SR = \frac{(APC\text{-}R\text{-}SR)_{specimen}}{(APC\text{-}R\text{-}SR)_{control\ plasma}}.$$

7. The process of claim 6, wherein a standardized ratio where n-APC-R-RS>0.80 generally indicates that said test specimen has no resistance to the activated protein C, and a standardized ratio where n-APC-R-SR<0.80 generally indicates that said test specimen does have resistance to the activated protein C.

8. The process of claim 1, wherein the normal plasma used as the control is a pool of normal human plasmas.

9. The process of claim 1, wherein in step (1), said test specimen is diluted to a concentration greater than or equal to 1:20 v/v and said reactant is a human plasma deficient in factor V enriched with phospholipids and said mixture is incubated for 4 minutes at 37° C.

10. The process of claim 9, wherein said test specimen is diluted with Owen-Koller buffer.

11. The process of claim 1, wherein in step (4), said normal plasma is a pool of normal human plasmas.

12. The process of claim 1; further comprising normalizing of the correlation of resistance to activated protein C by comparing the coagulation time (T) obtained in step (3, ii) with a reference coagulation time ($T_0$) determined by experiment, where
   $T<T_0$ generally indicates that the test specimen of human plasma has resistance to the activated protein C, and
   $T>T_0$ generally indicates that the test specimen of human plasma has no resistance to the activated protein C.

13. The process of claim 12, wherein $T_0$ has a value of about 110 seconds.

14. The process of claim 12, wherein $T_0$ is 110±10 s, whereby:
   when T>120 s, said test specimen has no resistance to the activated protein C, and
   when T<100 s, said test specimen does have resistance to the activated protein C, an interval between 100s≦T≦120 s being the interval of doubt.

15. A process for determining resistance to activated protein C of a test sample of human plasma, comprising the steps of:

(1) mixing together
   (a) said test specimen of human plasma,
   (b) a reactant deficient in factor V which provides at least most of coagulation factors other than factor V, and
   (c) venom of *Crotalus viridis helleri* which specifically activates factor X to Xa,
and incubating the resulting mixture of (a), (b) and (c) for one minute at a temperature of between 10 and 45° C.;

(2) introducing $Ca^{2+}$ and exogenic activated protein C into said mixture of step (1);

(3) measuring a coagulation time (T); and (4) correlating resistance to activated protein C by comparing the measured coagulation time (T) with an experimentally determined reference coagulation time ($T_0$) having a value of about 110 seconds, where $T<T_0$ indicates that said test specimen has a resistance to activated protein C, and $T>T_0$ indicates that said test specimen has no resistance to activated protein C, wherein initiation of coagulation is by means of activating factor X to Xa by said venom in the presence of a mixture of $Ca^{2+}$ and exogenic APC.

16. The process of claim 15, wherein $T_0$ is 110 ±10 s, whereby:
   when T>120 s, said test specimen has no resistance to the activated protein C, and
   when T<100 s, said test specimen does have resistance to the activated protein C, an interval between 100s $\leq T \leq 120$ s being the interval of doubt.

17. The process of claim 15, wherein said mixture of step (1) is incubated for 3 to 5 minutes at a temperature of between 35 to 40° C.

18. The process of claim 15, wherein said mixture of step (1) is incubated for 4 minutes at a temperature of 370° C.

* * * * *